US007563254B2

(12) United States Patent
DeLegge

(10) Patent No.: US 7,563,254 B2

(45) Date of Patent: Jul. 21, 2009

(54) UNIVERSAL PERCUTANEOUS ENDOSCOPIC GASTROSTOMY TUBE

(76) Inventor: Rebecca DeLegge, 3233 Cotton Field Dr., Mt. Pleasant, SC (US) 29466

( * ) Notice: Subject to any disclaimer, the term of this patent is extended or adjusted under 35 U.S.C. 154(b) by 835 days.

(21) Appl. No.: 10/760,926

(22) Filed: Jan. 20, 2004

(65) Prior Publication Data

US 2005/0020875 A1 Jan. 27, 2005

Related U.S. Application Data

(60) Provisional application No. 60/440,901, filed on Jan. 17, 2003, provisional application No. 60/452,403, filed on Mar. 6, 2003.

(51) Int. Cl.
*A61M 5/00* (2006.01)

(52) U.S. Cl. ....................................... 604/264; 604/910

(58) Field of Classification Search ................. 600/114, 600/129; 604/171, 164.01, 264, 270, 910
See application file for complete search history.

(56) References Cited

U.S. PATENT DOCUMENTS

| | | | | | |
|---|---|---|---|---|---|
| 4,824,435 | A * | 4/1989 | Giesy et al. | ................. | 604/500 |
| 5,807,314 | A * | 9/1998 | Ross et al. | .................. | 604/500 |
| 5,904,648 | A * | 5/1999 | Arndt et al. | ................. | 600/120 |

* cited by examiner

*Primary Examiner*—Kevin C Sirmons
*Assistant Examiner*—Deanna K Hall
(74) *Attorney, Agent, or Firm*—B. Craig Killough; Ernest B. Lipscomb, III

(57) ABSTRACT

A universal percutaneous endoscopic gastrostomy (PEG) tube that may be used with either the push or the pull insertion method. A loop extends from the tube. A void is formed in the tube at or near the proximal end of the tube. The void communicates with the internal void that acts as a conduit for material that is transported by the tube. The tube of the invention provides the option of changing technique from push method to pull method, or from pull method to push method. The device provides a mechanism at the tip or at mid catheter, thereby allowing for change over of method.

2 Claims, 5 Drawing Sheets

UNIVERSAL PERCUTANEOUS ENDOSCOPIC GASTROSTOMY TUBE

Applicant Claims priority from U.S. Provisional Application Ser. No. 60/440,901 filed Jan. 17, 2003 and from U.S. Provisional Application Ser. No. 60/452,403 filed Mar. 6, 2003.

FIELD OF THE INVENTION

This invention relates to a percutaneous endoscopic gastrostomy tubes generally, and is more specifically directed to a device and methods for positioning a percutaneous endoscopic gastrostomy (PEG) tube.

BACKGROUND OF THE INVENTION

PEG tubes are known and used in the art. PEG tubes are used to provide nutrition to patients who are unable to swallow, or are otherwise unable to receive food by normal bodily processes due to disease or injury. PEG tubes may be positioned within the stomach, or they may be positioned within the intestine.

Two predominant methods for positioning PEG tubes are the Ponsky-Gauderer 'pull' technique and the Sachs-Vine 'push' technique. The pull and push techniques differ only in the method of insertion of the gastrostomy tube. In the pull technique, the proximal portion of the tube is pulled through the mouth, esophagus, stomach and abdominal wall; whereas, during the push technique the tube is pushed over a guide wire.

Currently, the device that is used for the push method differs from the device that is used for the pull method. Since the method is a matter of physician preference and training[1], hospitals keep a supply of each of the devices in inventory. This necessity represents an inventory expense to the hospital, and the administrative burden of tracking inventory.

[1] These techniques have been shown to be substantially equivalent in safety and insertion success rates In particular, the device that is used for the pull technique has a wire loop formed on one end that enables the PEG tube to be connected to an insertion wire and pulled through the mouth and esophagus, and into the stomach. The device that is used for the push technique has no such wire loop; rather, the insertion wire is inserted into the orifice in the tube, through an opening at the proximal end of the tube, and the tube is pushed along the wire, which acts as a guide, until the tube is in position.

SUMMARY OF THE INVENTION

The present invention is a universal PEG tube that may be used with either the push or the pull insertion method. A loop extends from an end the tube. A void is formed in the tube at or near the proximal end of the tube. The void communicates with the internal void that acts as a conduit for material that is transported by the tube.

DESCRIPTION OF THE PREFERRED EMBODIMENT

Figure 1A:
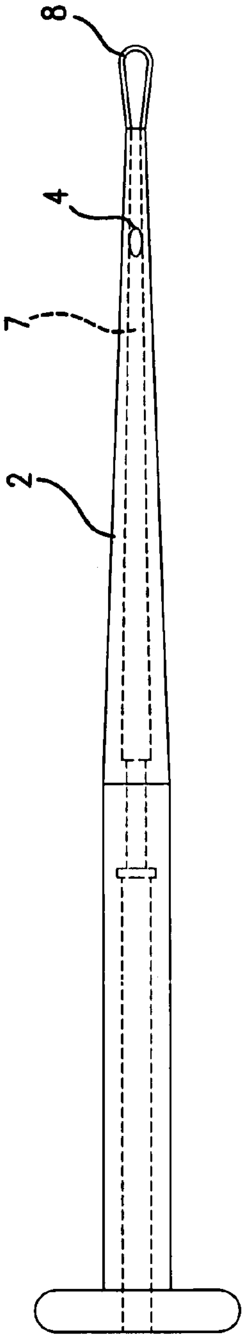
FIG. 1*a* shows a partial view of a first embodiment of the device.
Figure 1B:
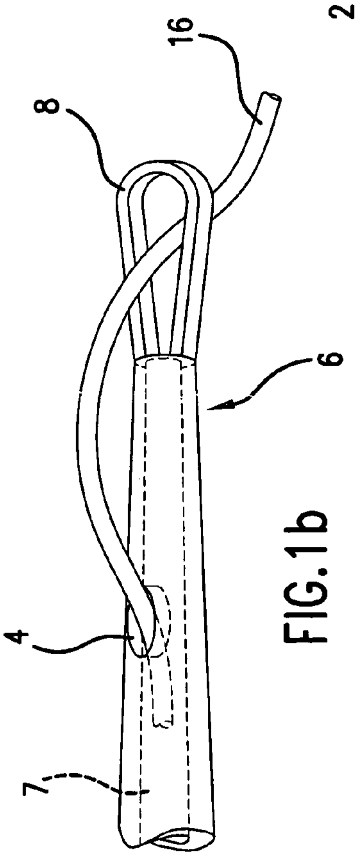
FIG. 1*b* shows an isolation of a proximal end of the first embodiment of the device.
Figure 1C:
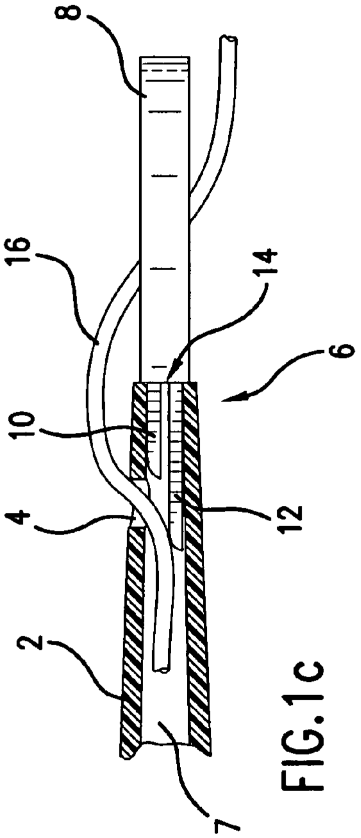
FIG. 1*c* shows an enlarged and sectioned proximal end of the first embodiment of the device

Referring now to FIGS. 1*a*-1*c*, the first embodiment of the universal PEG tube 2 has a void 4 that is formed near the proximal end 6 of the tube. The tube has an elongated lumen 7 that extends though a central portion of the tube. The lumen is preferred to be tapered toward the proximal end of the tube. The tube may be tapered toward the proximal end of the tube.

Void 4 is formed in a side of the tube, such as by skiving the tube, or by molding a void in the tube during the tube formation process, or by forming a void in the tube after the tube is produced. A loop 8 is present within a void that is formed in the proximal end of the PEG tube. In the preferred embodiment, the loop has a pair of generally parallel legs 10, 12 that extend from the loop. The generally parallel legs are inserted into the void 14 which forms the conduit for the tube, and through the void, and which is present in the proximal end of the tube. In the preferred embodiment, the generally parallel legs are of unequal length, with the longer leg 12 extending at least to the void 4, and positioned within the tube so that it is generally opposite the void. The shorter leg does not extend to the void, since it would interfere with use of the void if it were as long as the longer leg. The longer leg reinforces the tube at the void, and prevents the tube from being punctured or otherwise damaged when the wire guide is inserted through the void and into the conduit of the tube. Without the longer leg, the wire may inadvertently be forced through the void, into the conduit, and puncture the opposite side of the tube, which would reduce the structural integrity of the tube, if not irreparably damage it. The hole in loop 8 the void 4 are generally perpendicular to the lumen.

The embodiment shown in is used according to the push method as demonstrated in FIGS. 1*b*-*c*. The insertion or guide wire 16 is threaded through the loop, and into the void. The PEG tube is then pushed along the wire, which acts as a guide, until the PEG tube is in the desired position within the stomach or intestine.

The embodiment shown in FIG. 1 is used according to the pull method as shown in FIG. 5 and FIGS. 6*a* through 6*c*. The insertion wire 18 is threaded through the loop, and over the enlarged opposite end 20 of the tube, and the tube is pulled through the loop of the insertion wire so that a knot is formed between the loop and the insertion wire. The PEG tube is then pulled into place by means of the insertion wire.

Figure 2:
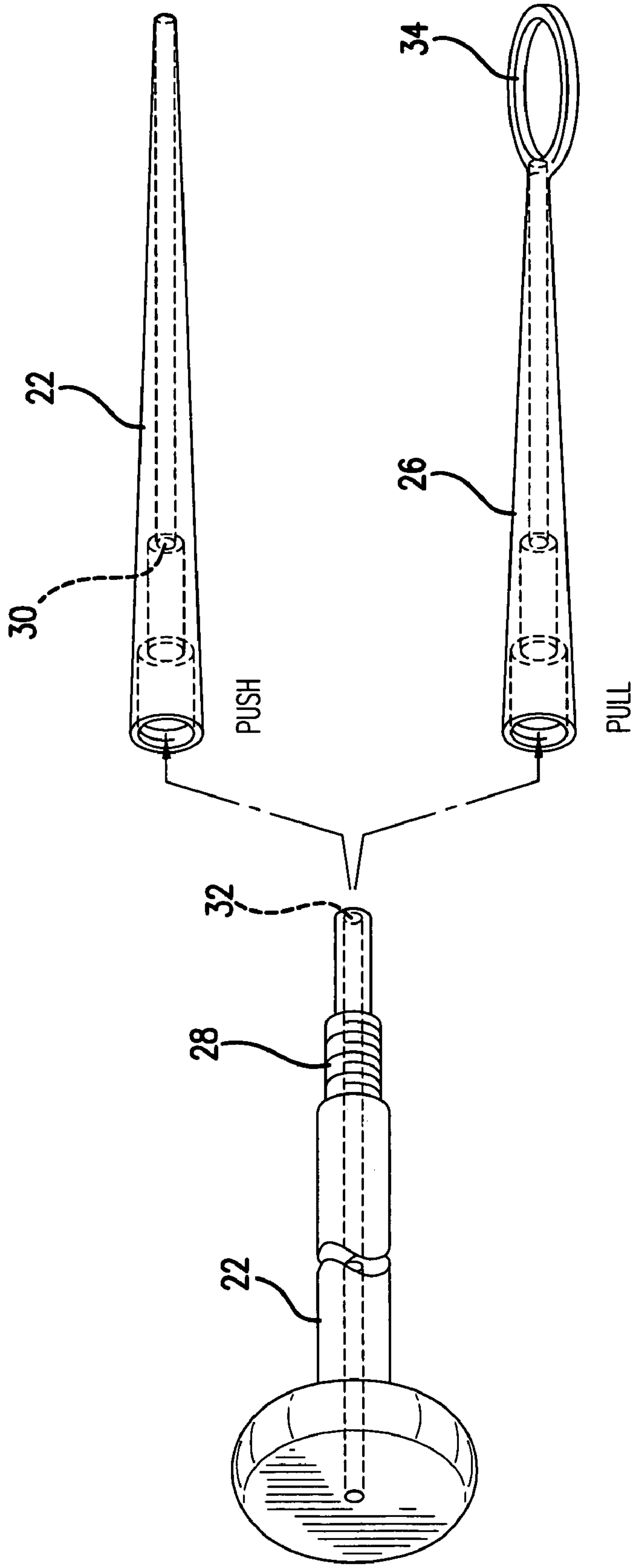
FIG. 2 shows a second embodiment of the device.

FIG. 2 shows an additional embodiment of the device. The PEG tube 22 of has a push adapter 24 and a pull adapter 26. The adapter is selected according to the method to be used. The adapters engage the PEG tube by a threaded engagement 28 or other attachment means. If the push method is to be used, then the push adapter is threaded onto the proximal end of the PEG tube. The push adapter has a concentric longitudal void 30 that aligns with the opening 32 in the proximal end of the PEG tube and aligns with the conduit of the PEG tube. The insertion wire may be threaded into the void in the end of the push tube, and the PEG tube pushed along the guide wire until the PEG tube is properly positioned.

If the pull method is to be used with the embodiment shown in FIG. 2, the pull adapter is threaded or other attachment means onto the PEG tube. A loop 34 is provided in the end of the pull adapter, and the insertion wire may be tied to the PEG tube in the manner shown in FIG. 5 and FIGS. 6*a* through 6*c* for insertion.

Figure 3:
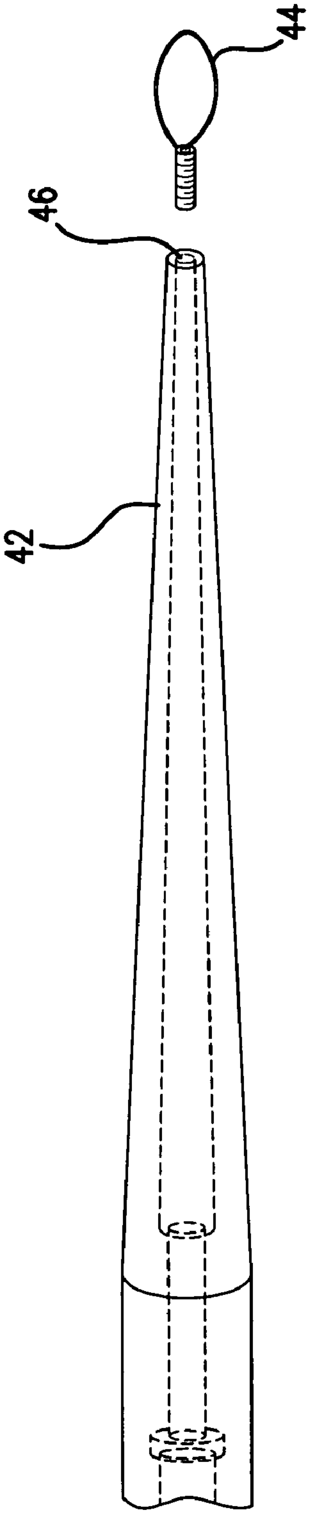
FIG. 3 shows a third embodiment of the device.

FIG. 3 shows a third embodiment of the universal PEG tube 42, wherein a loop 44 is provided on the end of the PEG tube. Also, a void 46 is present in the proximal end of the PEG tube. If the push method is to be used, the insertion wire is inserted through the void, and the PEG tube is pushed along the wire which acts as a guide. If the pull method is to be used, the insertion wire is tied to the loop as discussed above.

Figure 4:
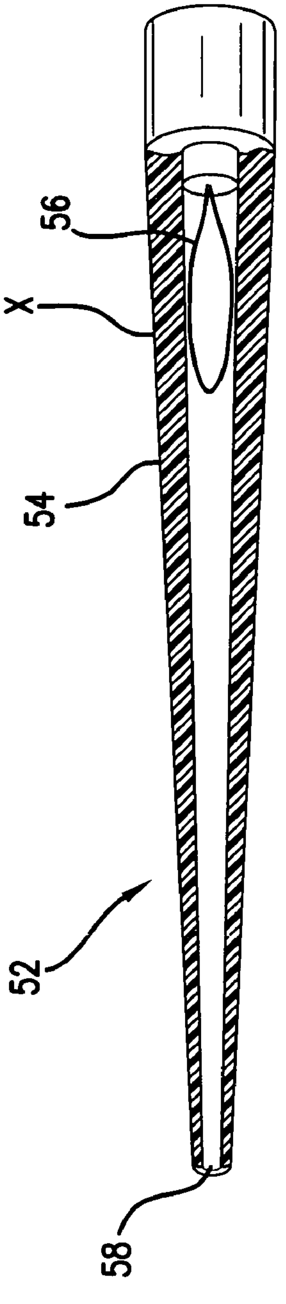
FIG. 4 shows a fourth embodiment of the device.
Figure 5:
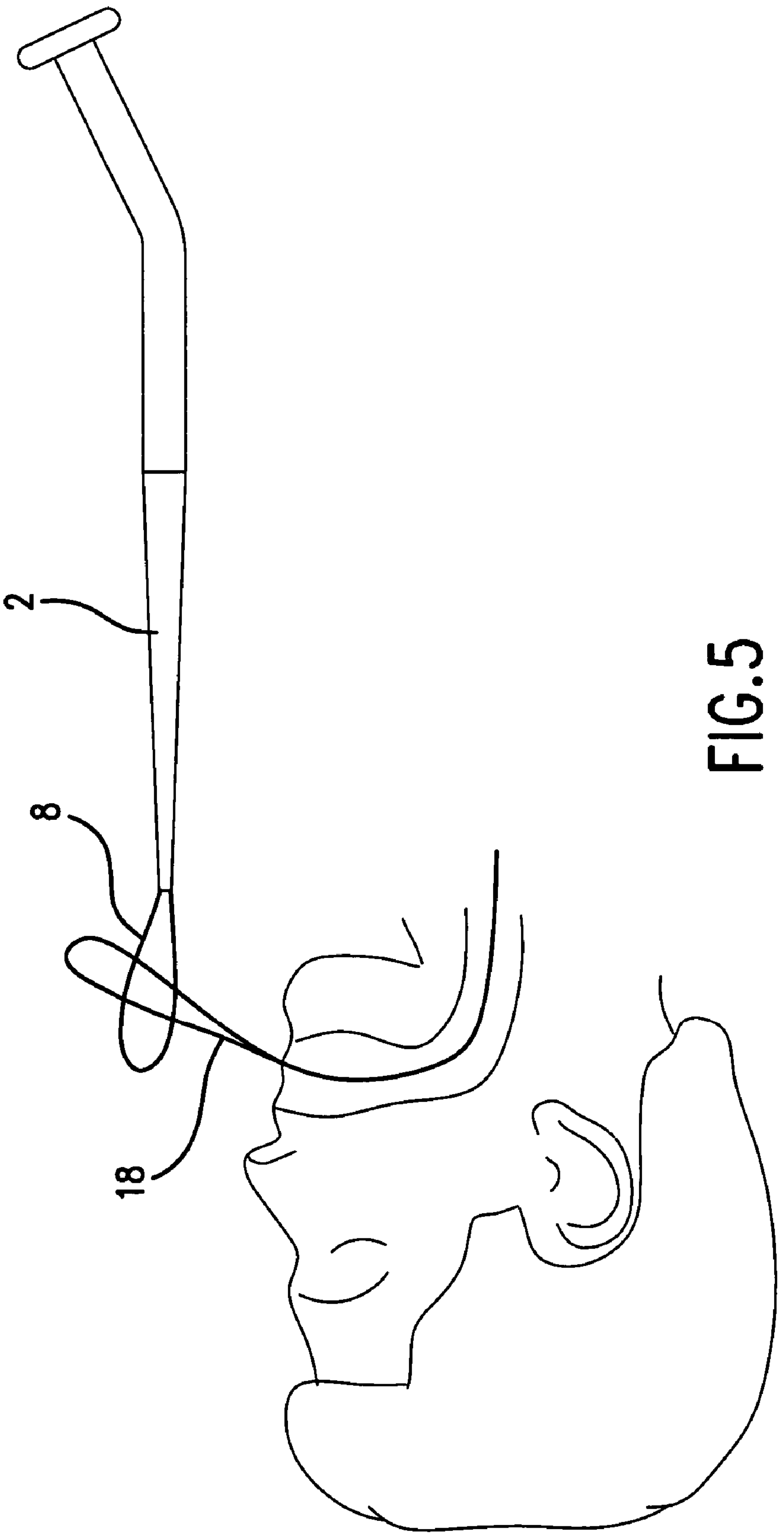
FIG. 5 shows a PEG tube that is being tied to an insertion wire for use with the pull method.
Figures 6A, 6B, 6C:
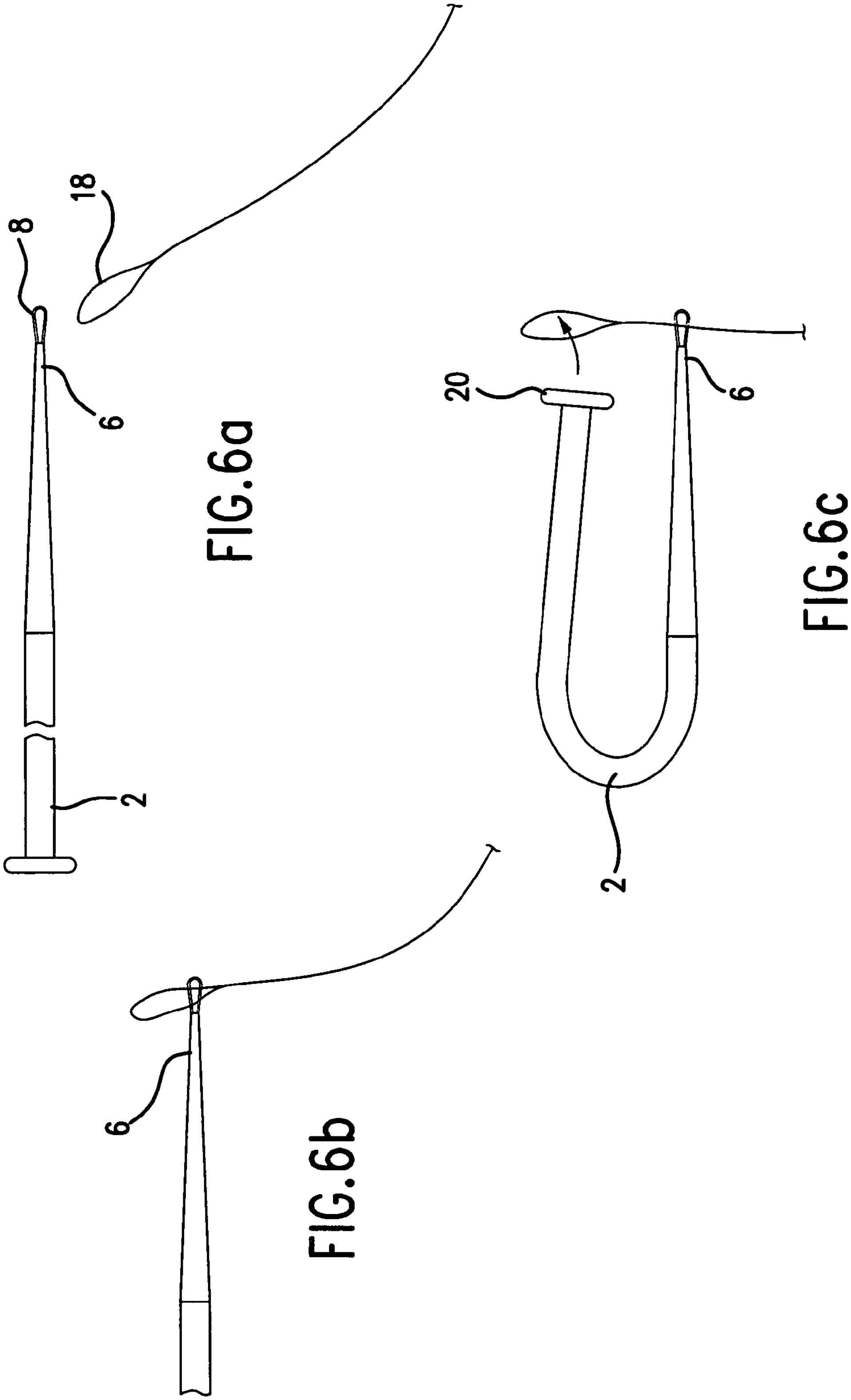
FIGS. 6*a*-6*c* show a series of steps for tying a PEG tube to an insertion wire for use with the pull method.

FIG. 4 shows an embodiment of the PEG tube 52 having an outer sheath 54 that covers the loop 56 which may be used for the pull method. With a sheath positioned over the loop, the device may be used as a PEG tube for the push method. The guide wire is inserted through a void 58 in the end of the sheath. Void 58 communicates with the conduit of the PEG tube, and allows the guide wire to enter the PEG tube. When used with the pull method, the sheath may be removed, so that the loop is available for tying the insertion wire to the PEG tube. Alternatively, the sheath may be circumscribed with a knife near X to expose the loop, so that the loop is available for attachment to the insertion wire.

What is claimed is:

1. A percutaneous endoscopic gastrostomy tube comprising an elongated tube, said elongated tube having an elongated lumen therein and having void formed in the side wall of said tube near a proximal end of said tube that communicates with said lumen and with an exterior of said tube, said tube having a loop that extends from said proximal end, said loop having a pair of generally parallel legs that extend from said loop into said lumen, said legs being of unequal length, with the longer leg extending at least to the void and positioned so that it is generally opposite said void, wherein said lumen and said void are formed to traverse a guide wire that extends into said void and said lumen.

2. A percutaneous endoscopic gastrostomy tube comprising an elongated tube, said elongated tube having an elongated lumen therein and having void formed in the side wall of said tube near a proximal end of said tube that communicates with said lumen and with an exterior of said tube, said tube having a loop that extends from said proximal end, wherein said lumen and said void are formed to traverse a guide wire that extends into said void and said lumen, and said loop having a pair of generally parallel legs that extend from said loop into said lumen, said legs being of unequal length, with the longer leg extending at least to the void and positioned so that it is generally opposite said void.

* * * * *